United States Patent [19]

Wettling et al.

[11] Patent Number: 5,530,147

[45] Date of Patent: Jun. 25, 1996

[54] SELECTIVE HYDROGENATION OF AROMATIC GROUPS IN THE PRESENCE OF EPOXY GROUPS

[75] Inventors: Thomas Wettling; Ludwig Schuster, both of Limburgerhof; Jochem Henkelmann, Mannheim, all of Germany

[73] Assignee: BASF Aktiengesellschaft, Ludwigshafen, Germany

[21] Appl. No.: 422,905

[22] Filed: Apr. 17, 1995

[30] Foreign Application Priority Data

Apr. 22, 1994 [DE] Germany ............... 44 14 090.8

[51] Int. Cl.[6] ................ C07D 301/00; C07D 303/23
[52] U.S. Cl. ............................. 549/540; 549/560
[58] Field of Search ............................. 549/540

[56] References Cited

U.S. PATENT DOCUMENTS

| | | | |
|---|---|---|---|
| 3,336,241 | 8/1967 | Shokal. | |
| 3,966,636 | 6/1976 | Jenkins et al. | 549/540 |
| 4,847,394 | 7/1989 | Schuster. | |
| 5,391,773 | 2/1995 | Puekette | 549/540 |

FOREIGN PATENT DOCUMENTS

| | | |
|---|---|---|
| 90816/82 | 11/1982 | Australia. |
| 545154 | 6/1993 | European Pat. Off.. |
| 3629632 | 3/1988 | Germany. |
| 3919228 | 12/1990 | Germany. |
| 402743 | 11/1933 | United Kingdom. |

OTHER PUBLICATIONS

Muetterties et al., *Acc. of Chem. Res.*, "Catalytic hydrogenation . . . ", vol. 12, No. 9, Sep. 1979, pp. 324–331.

Fache et al., *Tetra. Letters*, vol. 36, No. 6, Feb. 1995, pp. 885–888.

*Primary Examiner*—Joseph E. Evans
*Attorney, Agent, or Firm*—Keil & Weinkauf

[57] ABSTRACT

A process for the selective hydrogenation of aromatic groups of organic molecules carrying at least one aromatic group and one epoxy group with hydrogen in the presence of a ruthenium-containing catalyst, in which a homogeneous ruthenium catalyst is used which can be prepared by reducing the ruthenium compound with a metal having a redox potential of from −0.75 to 2.5 V, a boron hydride, an aluminum hydride, an aluminum alkyl compound, a lithium alkyl compound, or a lithium aryl compound in the presence of an ether.

6 Claims, No Drawings

SELECTIVE HYDROGENATION OF AROMATIC GROUPS IN THE PRESENCE OF EPOXY GROUPS

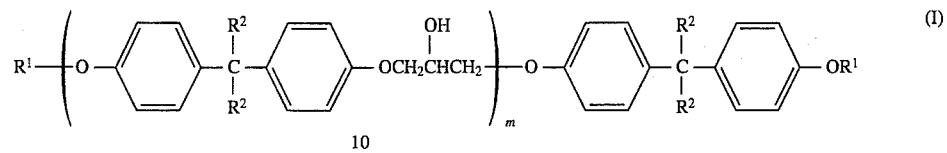

The present invention relates to an improved process for the selective hydrogenation of aromatic groups of organic molecules carrying at least one aromatic group and one epoxy group with hydrogen in the presence of a ruthenium-containing catalyst.

U.S. Pat. No. 3,336,241 teaches the hydrogenation of aromatic epoxy compounds with heterogeneous rhodium and ruthenium catalysts. The selectivity of these catalysts is not satisfactory, since during the hydrogenation of the aromatic groups epoxy groups also react with hydrogen to a considerable extent.

A substantially more selective catalyst is ruthenium oxide hydrate, such as is described in DE-A 3,629,632 and DE-A3,91 9,228 for the hydrogenation of di[glycidoxiphenyl]methane and 2,2-di[glycidoxiphenyl]propane respectively.

Since this catalyst is, however, usually used in the form of a solvent-moist paste, the accurate dosage thereof causes industrial problems.

It was thus an object of the present invention to provide a process using catalysts which on the one hand favor hydrogenation of the aromatic groups at maximum selectivity and on the other hand are easy to meter. Another object was to find catalysts which can be manufactured in a simple manner.

Acccordingly, we have found the process defined above, wherein a homogeneous ruthenium catalyst is used which can be prepared by reducing the ruthenium compound with a metal having a redox potential of from −0.75 to 2.5 V, a boron hydride, an aluminum hydride, an aluminum alkyl compound, a lithium alkyl compound, or a lithium aryl compound in the presence of an ether.

Suitable starting compounds are all such organic molecules which carry at least one aromatic group and one epoxy group. The compounds concerned may be monomeric, oligomeric or polymeric compounds. Examples of suitable starting compounds for the process of the invention are the following individual substances and classes of substances:

Products of the reaction of bisphenol A or bisphenol F with epichlorohydrin

Bisphenol A or bisphenol F and epichlorohydrin can be caused to react with bases in known manner (eg, *Ullmann's Encyclopedia of Industrial Chemistry*, 5th Ed., VCH (1987) Vol. A9) to produce glycidyl ethers of the general formula I in which $R^1$ stands for

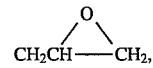

$R^2$ stands for hydrogen or a methyl group and m stands for zero to 40

Phenol- and cresol-epoxy novolaks

Novolaks of the general formula II are obtainable by the acid-catalyzed reaction of phenol and cresol respectively and epoxydization of the products of the reaction (cf, eg, bis[4-(2,3-epoxypropoxy)phenyl]methane):

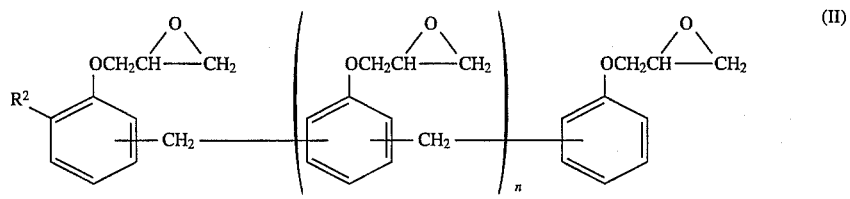

in which $R^2$ stands for hydrogen or a methyl group and n for 0 to 40

Glycidyl ethers of products of the reaction of phenol with an aldehyde

Glycidyl ethers are available by the acid-catalyzed reaction of phenol with aldehydes followed by epoxydization with epichlorohydrin, eg, 1,1,2,2-tetrakis[4-(2,3-epoxypropoxy)phenyl]ethane is available from phenol and glyoxal.

Aromatic glycidylamines

Examples thereof are as follows: the triglycidyl compound of p-aminophenol, 1-(2,3-epoxypropoxy)-4-[N,N-bis(2,3-epoxypropyl)amino]benzene, and the tetraglycidyl compound of methylenediamine bis{4-[N,N-bis(2,3-epoxypropyl)amino]phenyl}methane Other specific examples are:

1,1,2,2-tetrakis[4-(2,3-epoxypropoxy)phenyl]ethane, isomers of tris[4-(2,3-epoxypropoxy)phenyl]methane, 2,5-bis [(2,3-epoxypropoxy)phenyl]octahydro-4,7-methano- 5H-indene.

Preferred starting compounds are di[p-glycidoxyphenyl] methane and 2,2-di-[p-glycidoxyphenyl]-propane and oligomers of these compounds.

Suitable catalysts for the process of the invention are homogeneous ruthenium catalysts. These are obtained by the reduction of ruthenium compounds. Examples of particularly suitable ruthenium compounds are Ru(III) compounds such as ruthenium trichloride and ruthenium acetylacetonate.

The aforementioned ruthenium compounds can be caused to react with a series of reducing agents to form homogeneous catalysts. Specific examples thereof are:

metals having a redox potential of from −0.75 to −2.5 V such as Mg, Al, Zn and Na, which are preferably used as a powder, boron hydrides such as sodium borohydride, aluminum hydrides, for example dialkyl aluminum hydrides such as dibutyl aluminum hydride, and alanates such as lithium aluminum hydride, aluminum alkyl compounds such as triethyl aluminum, lithium alkyl compounds such as butyllithium and lithium aryl compounds such as phenyllithium.

The reducing agents are caused to react with the ruthenium compound usually at temperatures of from 20° to 100° C. for from 0.5 to 20 hours. During this process, generally at least 1 reduction equivalent of the said compounds is used per equivalent of the ruthenium compound used, alternatively, large excesses of reducing agents can be used.

The reduction is carried out in the presence of an ether. Particularly suitable ethers are aliphatic $C_3$–$C_{30}$ ethers such as tetrahydrofuran, dioxane, glycol dimethyl ether, formaldehyde dimethylacetal, acetaldehyde dimethylacetal, diethyl ether and methoxypropanol. These ethers stabilize the homogeneous catalyst by complexing the reduced ruthenium compounds. The amount of ether used can be from 30 to more than 99 wt %, based on the ruthenium compound used.

In a preferred embodiment the reduction of the ruthenium compound is carried out in the presence of the starting compound to be hydrogenated, so that the hydrogenation can be carried out without having to transfer individual components.

The hydrogenation is carried out in a manner known per se. To this end, the starting compound is mixed with the catalyst—if this is not one which has been prepared in the presence of the starting compound—and optionally with a solvent. A suitably solvent is preferably the ether in the presence of which the reduction of the ruthenium compound takes place. The amounts are generally from 5 to 90 wt %, based on the reaction mixture. Hydrogenation is effected with hydrogen, the pressure usually being from 80 to 320 bar, preferably from 200 to 310 bar. The temperature of reaction is generally in the region of from 30° to 80° C., preferably from 40° to 70° C. The reaction is generally complete after from 2 to 10 hours. To effect purification of the reaction mixture it can then be depressurized to standard pressure, after which the solids precipitated during the reaction can be separated and all of the volatile constituents can be removed by distillation.

The process of the invention allows for selective hydrogenation of aromatic groups in the presence of epoxy groups. The catalysts used for this purpose can be easily prepared in the reaction mixture. The ruthenium compound required for the preparation of the catalysts can also be metered in in small amounts, accurately and simply.

The end products are useful as lightproof coating compositions, casting resins and laminates.

EXAMPLES

Example 1

24.4 g of ruthenium trichloride hydrate (content of ruthenium 10 g) were refluxed in 1000 g of tetrahydrofuran under nitrogen together with 75 g of magnesium powder for 5 h and the mixture was subsequently filtered.

33.2 g of the resulting solution were hydrogenated in an autoclave using 75 g of a bisglycidyl ether of a phenol/formaldehyde condensate (bis[ 4-(2,3-epoxypropoxy)-phenyl]methane having an epoxide equivalent value of 168) and 50g of tetrahydrofuran under a pressure of 250 bar rising from 50° to 70° C. over a period of 8 h. Following filtration and removal, by distillation, of the volatile constituents, there remained 76 g of a colorless epoxy resin, whose aromatics content had been hydrogenated to an extent of 93.5% (as determined by $^1$H-NMR-spectroscopy). The epoxyde equivalent weight (determined according to ASTM D 1652-88) was 184.

Example 2

2.48 g of ruthenium trichloride hydrate (1.02 g calculated as ruthenium), 7.5 g of magnesium powder, 1 kg of the bisglycidyl ether characterized in Example 1, and 1 kg of tetrahydrofuran were stirred for 2 h at 70° C. under nitrogen. Hydrogenation was then carried out over a period of 14 h under a pressure of 250 bar and a temperature of from 50° to 70° C. Following purification as in Example 1, there were isolated 1030 g of epoxy resin (degree of hydrogenation of the aromatics 93.3%, epoxyde equivalent weight 177).

Example 3

Example 2 was repeated except that 4.5 g of aluminum powder were used instead of magnesium powder. Yield: 1032 g (degree of hydrogenation of the aromatics content 100%, epoxyde equivalent weight 181).

Example 4

To 183 mg of ruthenium trichloride hydrate in 60 g of tetrahydrofuran there were added, at −50° C., 4.5 mL of a 20 wt % strength solution of dibutylaluminum hydride in hexane. At room temperature there were added 75 g of the bisglycidyl ether characterized in Example 1 and hydrogenation was carried out under a pressure of 250 bar and at a temperature of from 50° to 70° C.

Following the addition of 1 g of water (for the hydrolysis of excess hydride) and 1 g of activated charcoal, the effluent was filtered and the volatile constituents were removed by distillation. There were obtained 73 g of a slightly colored epoxy resin (degree of hydrogenation of the aromatics content 88.2%, epoxyde equivalent weight 179).

Example 5

490 mg of ruthenium trisacetylacetonate (100 mg calculated as ruthenium) were reduced in 20 mL of THF at 100° C. by the addition of 510 mg of triethyl aluminum (2.5 mL of a 25% strength solution in toluene).

There were then added 100 g of the bisglycidyl ether described in Example 1 and 80 mL of THF and the solution obtained was caused to react for 5 h at 70° C. under a hydrogen pressure of 250 bar.

Following purification as described in Example 4 there were obtained 103 g of a slightly colored epoxy resin (degree of hydrogenation of the aromatics content 91.3%, epoxyde equivalent weight 181).

Example 6 (reduction in the presence of a glycidyl ether)

2.5 g of ruthenium trichloride hydrate (1.02 g of ruthenium), 2.5 g of magnesium, 1 kg of the bisglycidyl ether characterized in Example 1 and 1 kg of THF were caused to react for 6 h at 70° C. under 250 bar of hydrogen. Following filtration and the removal, by distillation, of the volatile components there were isolated 1037 g of a colorless epoxy resin (quantitative hydrogenation of the aromatics content, epoxyde equivalent weight 178).

We claim:

1. A process for the selective hydrogenation of aromatic groups of organic molecules carrying at least one aromatic group and one epoxy group with hydrogen in the presence of a catalyst containing a ruthenium compound, wherein a homogeneous catalyst is used which is prepared by reducing the ruthenium compound with a metal having a redox potential of from −0.75 to 2.5 V, or with a boron hydride, an aluminum hydride, an aluminum alkyl compound, a lithium alkyl compound, or a lithium aryl compound, said reduction taking place in the presence of an ether.

2. A process as defined in claim 1, wherein di-[p-glycidoxyphenyl]methane or 2,2-di[p-glycidoxyphenyl]propane is hydrogenated.

3. A process as defined in claim 1, wherein the reduction of the ruthenium compound is carried out with magnesium or aluminum.

4. A process as defined in claim 1, wherein ruthenium trichloride is reduced.

5. A process as defined in claim 1, wherein the reduction of the ruthenium compound is carried out in the presence of the organic compound to be hydrogenated.

6. A process as defined in claim 1, wherein the reduction of the ruthenium compound is carried out in the presence of tetrahydrofuran, dioxane, glycol dimethyl ether, diethyl ether or methoxypropanol.

* * * * *

UNITED STATES PATENT AND TRADEMARK OFFICE
CERTIFICATE OF CORRECTION

PATENT NO.: 5,530,147

DATED: June 25, 1996

INVENTOR(S): WETTLING et al.

It is certified that error appears in the above-identified patent and that said Letters Patent is hereby corrected as shown below:

On the cover page, item [30], foreign application priority data " 44 14 090.8" should read --P 44 14 090.8--.

Signed and Sealed this

Seventeenth Day of September, 1996

*Attest:*

BRUCE LEHMAN

*Attesting Officer*  *Commissioner of Patents and Trademarks*